US007541360B2

(12) United States Patent
Doblhofer et al.

(10) Patent No.: US 7,541,360 B2
(45) Date of Patent: Jun. 2, 2009

(54) 4-AMINO-7,8-DIHYDROPTERIDINES, PHARMACEUTICAL COMPOSITIONS CONTAINING THEM AND THEIR USE FOR THE TREATMENT OF DISEASES WHICH ARE CAUSED BY AN INCREASED NITRIC OXIDE LEVEL

(75) Inventors: Robert Doblhofer, Putzbrunn (DE); Frank Tegtmeier, Grevenbroich (DE)

(73) Assignee: Vasopharm GmbH, Wurzburg (DE)

( * ) Notice: Subject to any disclaimer, the term of this patent is extended or adjusted under 35 U.S.C. 154(b) by 0 days.

(21) Appl. No.: 10/584,996

(22) PCT Filed: Dec. 30, 2003

(86) PCT No.: PCT/EP03/14970

§ 371 (c)(1),
(2), (4) Date: Jun. 11, 2007

(87) PCT Pub. No.: WO2005/063752

PCT Pub. Date: Jul. 14, 2005

(65) Prior Publication Data

US 2008/0027062 A1 Jan. 31, 2008

(51) Int. Cl.
*A61K 31/5025* (2006.01)
*C07D 475/08* (2006.01)
*C07D 239/50* (2006.01)
(52) U.S. Cl. .................. 514/249; 544/260; 544/323
(58) Field of Classification Search ................ 514/251, 514/249; 544/260
See application file for complete search history.

(56) References Cited

U.S. PATENT DOCUMENTS 3,242,178 A 3/1966 Elion
4,746,659 A * 5/1988 DeGraw et al. ............. 514/249
5,922,713 A 7/1999 Werner

FOREIGN PATENT DOCUMENTS

DE 44 18 097 A1 11/1995
EP 0 906 913 A1 4/1999
GB 2 240 041 A1 7/1991
WO WO 93/13055 7/1993
WO WO 95/32203 11/1995
WO WO 00/39129 7/2000
WO WO 01/21619 A1 3/2001

OTHER PUBLICATIONS

Christopherson, et al., J. Clin. Invest., vol. 100, No. 10, Nov. 1997, 2424-2429.*
Wolfe, et al., Ann. Pharmacother. Jan. 1995; 29(1): 36-46 (abst.).*
Akyurek, et al., Am. J. Path., vol. 149, 1981-1990, 1996 (5 page abstract).*
Parenti, et al., FASEB. J. (Apr. 27, 2001) 10.1096/fj.00-0503fje.*
NIH Medline Plus website, http://www.nlm.nih.gov/medlineplus/ency/article/000170.htm#top, downloaded Feb. 24, 2008.*
Nair, Journal of Organic Chemistry (1985), 50(11), 1879-84.*
Beilstein Record 1117249, Dated Nov. 29, 1988.*
Beilstein Record 5633531, dated Feb. 12, 1993.*
Beilstein Record 5613739, Dated Feb. 12, 1993.*
McCall, T. B. et al., "Identification of N-Iminoethyl-L-Ornithine as an Irreversible Inhibitor of Nitric Oxide Synthase in Phagocyctic Cells," Br. J. Pharmacol., vol. 102, No. 1. p. 234, (1991). (Abstract Only).
Misko, T. P. et al., "Selective Inhibition of the Inducible Nitric Oxide Synthase by Aminoguanidine," Eur. J. Pharmacol., vol. 233, No. 1, p. 119, (1993). (Abstract Only).
Moore, P. K. et al., "7-Nitro Indazole, an Inhibitor of Nitric Oxide Synthase, Exhibits Anti-Nociceptive Activity in the Mouse Without Increasing Blood Pressure," Br. J. Pharmacol., vol. 108, No. 2, p. 296, (1993). (Abstract Only).
Kwon, N. S. et al., "Reduced Biopterin as a Cofactor in the Generation of Nitrogen Oxides by Murine Macrophages," The Journal of Biological Chemistry, vol. 264, No. 34, pp. 20496-20501, (1989).
Giovanelli, J. et al., "Tetrhydrobiopterin, a Cofactor for Rat Cerebellar Nitric Does Not Function as a Reactant in the Oxygenation of Arg," Proc. Natl. Acad. Sci., vol. 88, No. 16, p. 7091, (1991). (Abstract Only).
Mülsch, A. et al., "Nitric Oxide Synthase in Native and Cultured Endothelial Cells: Calcium/Calmodulin and Tetrhdrobiopterin Are Cofactors," Journal of Cardiovascular Pharmacology, vol. 17, Suppl. 3, pp. S52-S56, (1991).
Sakai, N. et al., "Tetrahydrobiopterin is Required for Cytokine-Induced Nitric Oxide Production in a Murine Macrophage Cell Line (RAW 264)," Mol. Pharmacol., vol. 43, Issue 1, p. 6, (1993). (Abstract Only).
Klatt, P. et al., "Stimulation of Human Nitric Oxide Synthase by Tetrahydrobiopterin and Selective Binding of the Cofactor," FEBS Letters, vol. 305, No. 2, pp. 160-162, (1992).
Werner-Felmayer, G. et al., "$Ca^{2+}$/Calmodulin-Dependent Nitric Oxide Synthase Activity in the Human Cervix Carcinoma Cell Line ME-180," Biochem. J., vol. 289, pp. 357-361, (1993).
Hevel, J. M. et al., "Macrophage Nitric Oxide Synthase: Relationship Between Enzyme-Bound Tetrahydrobiopterin and Synthase Activity," Biochemistry, vol. 31, pp. 7160-7165, (1992).
Pfeiffer, S. et al., "Allosteric Modulation of Rat Brain Nitric Oxide Synthase by the Pterin-Site Enzyme Inhibitor 4-Aminotetrahydrobiopterin," Biochem. J., vol. 328, pp. 349-352, (1997).
Werner, E. R. et al., "Identification of the 4-Amino Analoque of Tetrahydrobiopterin as a Dihydropteridine Reductase Inhibitor and a Potent Pteridine Antagonist of Rat Neuronal Nitric Oxide Synthase," Biochem J., vol. 320, pp. 193-196, (1996).

(Continued)

*Primary Examiner*—Mark L Berch
*Assistant Examiner*—Cecilia M Jaisle
(74) *Attorney, Agent, or Firm*—Finnegan, Henderson, Farabow, Garrett & Dunner, L.L.P.

(57) ABSTRACT

The present invention relates to the area of NO synthase inhibition and, more particularly, relates to novel 4-amino-7,8-dihydropteridines, pharmaceutical compositions containing said compounds, and the use of said compounds in the treatment of a disorder characterized by a disturbed nitric oxide level.

4 Claims, No Drawings

OTHER PUBLICATIONS

Schircks, V. B. et al., "A New, Regiospecific Synthesis of L-Biopterine," Helvetica Chimica Acta, vol. 60, No. 1, pp. 211-214, (1977).

Futterman, S., "Enzymatic Reduction of Folic Acid and Dihydrofolic Acid to Tetrahydro-Folic Acid," J. Biol. Chem., vol. 228, pp. 1031-1038, (1957). (Abstract Only).

Fukushima, T. et al., "Nuclear Magnetic Resonance Studies of Some Biologically Active Dihydropterins," vol. 128, Issue 1, 1 page, (1968).

Pfleiderer, W. et al., "A Simple Synthetic Approach to 8-Substituted 5,6,7,8-Tetrathyro- and 7,8-Dihydropterins," Chem. Ber., vol. 104, pp. 2293-2312, (1971).

Andrews, K. J. M. et al., "A New Synthesis of Biopterin and L-Neopterin," Chemical Communications, pp. 120-121, (1968).

Hanaya, T. et al., "Pteridines CV Selective N(3)-and $O^4$-Alkylation of L-Biopterin: A Convenient Synthesis of 3-and $O^4$-Methyl-L-Biopterin and the Versatile $N^2$-(N,N-Dimethylaminomethylene)-N(3)-p-Nitrophenethyl-Protected L-Biopterin," Pteridines, vol. 6, No. 1, pp. 1-7, (1995).

Matter, H. et al., "Structural Requirements for Inhibition of the Neuronal Nitric Oxide synthase (NOS-I): 3D-QSAR Analysis of 4-Oxo-and 4-Amino-Pteridine-Based Inhibitors," J. Med. Chem., vol. 45, No. 14, pp. 2923-2941, (2002).

Knipp, M. et al., "A Colorimetric 96-Well Microtiter Plate Assay for the Determination of Enzymatically Formed Citrulline," Anal Biochem., vol. 286, No. 2, pp. 257-264, (2000). (Abstract Only).

Taylor, E. C. et al., "Pteridines. XXIX. An Unequivocal Route to 2,4-Diamino-6-Substituted Pteridines," Journal of the American Chemical Society, vol. 95, No. 19, pp. 6413-6418, (1973).

Kwee, S. et al., "Electrochemistry of Some Substituted Pteridines," Biochimica et Biophysica Acta, vol. 297, No. 2, p. 285-296, (1973). (Abstract Only).

Zimmerman, M. et al., "Inhibitors of Folate Biosynthesis. 1. Inhibition of Dihydroneopterin Aldolase by Pteridine Derivatives," Journal of Medicinal Chemistry, vol. 20, No. 9, pp. 1213-1215, (1977). (Abstract Only).

Al-Hassan et al., "2,4-Diamino-7,8-dihydro-6,7,7-trimethylpteridine;" J. Chem. Soc. Perkin Trans 1, pp. 2145-2150, (1985).

Al-Hassan et al., "2,4-Diamino-8-benzyl-7,8-dihydro-6,7,7-trimethylpteridine," J. Chem. Soc. Perkin Trans 1, pp. 2145-2150, (1985).

Chaykovsky et al., "6-methyl-7,8-dihydro-pteridine-2,4-diamine," J. Org. Chem., vol. 40, p. 145, (145).

European Search Report dated Sep. 10, 2007.

* cited by examiner

4-AMINO-7,8-DIHYDROPTERIDINES, PHARMACEUTICAL COMPOSITIONS CONTAINING THEM AND THEIR USE FOR THE TREATMENT OF DISEASES WHICH ARE CAUSED BY AN INCREASED NITRIC OXIDE LEVEL

CROSS REFERENCE TO RELATED APPLICATIONS

This application is a national phase application based on PCT/EP2003/014970, filed Dec. 30, 2003, the content of which is incorporated herein by reference.

The present invention relates to the area of NO synthase inhibition and, more particularly, relates to certain 4-amino-7,8-dihydropteridines, pharmaceutical compositions containing them, and the use of said compounds in the treatment and/or prevention of a disorder characterized by increased NO levels.

Nitric oxide (NO) plays an important part in all sorts of physiological processes (see, for example, R. Henning, Nachr. Chem. Tech. Lab. 41 (1993), 413; H. H. H. W. Schmidt et al., Biochim. Biophys. Acta 1178 (1993), 153). It has, for example, a relaxing effect on the smooth vascular musculature and in this way is substantially involved in the regulation of blood pressure. It controls blood clotting via inhibition of platelet aggregation, and it is involved, for example, as a neurotransmitter in the brain in the building up of long-term memory. NO also functions as a messenger substance in the NANC nerves of the peripheral nervous system. The cytotoxic action of NO is utilized by macrophages for defense against infection.

Endogenous NO is formed from arginine with the aid of at least three different NO synthase (NOS) isoenzymes (see, for example, J. F. Kerwin, Jr. and M. Heller, Med. Res. Rev. 14 (1994), 23). They differ with respect to their localization in the body, their regulability by $Ca^{2+}$/calmodulin and their inducibility by endotoxins and cytokines. The constitutive, calcium-dependent NO synthases are found, for example, in endothelium (Type III) and in the brain (Type I) and are involved there in the regulation of blood pressure and coagulation and in conduction processes. The cytokine-inducible, calcium-independent isoform (Type II) occurs in macrophages, smooth muscle cells and hepatocytes. It is able, over the long term, to produce relatively large amounts of NO and is held responsible for inflammatory processes and the cytotoxic activity of the macrophages.

A disturbed NO balance results in serious disorders and damage. Thus excessive formation of NO in septic or hemorrhagic shock leads to massive pathological blood pressure decreases. Excess NO production is involved in the formation of type 1 diabetes and atherosclerosis and also appears to be responsible for glutamate-induced neurotoxicity after cerebral ischemia. High NO concentrations can moreover lead to DNA damage as a result of deamination of cytosine. Examples of disorders which are caused indirectly or directly by a lack of endogenous NO are arterial high blood pressure, hemostasis disorders, coronary heart disease and erectile dysfunction.

The attempt to use modulation of NO production for the treatment of these syndromes has until now only been realized with the aid of arginine analogs (GB-A-2240041; WO-A-93/13055). Various pteridine derivatives were discussed as potential inhibitors of NO synthases (see e.g., N-iminoethylornithine in Mc Call et al., Br. J. Pharmacol. 102 (1991) 234; aminoguanidine in T. P. Misko et al., Eur. J. Pharmacol. 233 (1993) 119; and 7-nitroindazole in P. K. Moore et al., Br. J. Pharmacol. 108 (1993) 296). All of these approaches for inhibiting NOS rely on competitive binding to the L-arginine binding site of the NOS enzyme.

Furthermore, inhibition of NO production by 6R-5,6,7,8-tetrahydrobiopterin analogs (BH4-analogs) was also discussed in several scientific publications (see e.g., Stuehr et al., J. Biol. Chem. 264 (1989) 20496; Giovanelli et al., Proc. Natl. Acad. Sci. 88 (1991) 7091; Mülsch and Busse, J. Cardiovasc. Pharmacol. 20, 17 (1991) 52; Sakai et al., Mol. Pharmacol. 43 (1992) 6; Werner et al., FEBS Letters 305 (1992) 160; Wachter et al., Biochem. J. 289 (1993) 357; and Hevel and Marletta, Biochemistry 31 (1992) 7160. Accordingly, 6S-BH4, 7-R/S-BH4, 6-methyl-5,6,7,8-tetrahydropteridine and dihydrobiopterin are capable to partially replace the natural cofactor, whereas biopterin, 6,7-dimethyl-5,6,7,8-tetrahydropteridine, tetrahydrofolic acid, dihydrofolic acid, folic acid, tetrahydroneopterin, dihydroneopterin, neopterin, methotrexate, pterine, 6-hydroxymethylpterine, xanthopterine and isoxanthopterine have not shown any significant effects.

Pfeiffer et al. (Biochem. J. 328 (1997) 349, WO 01/21619, and WO 00/39129 describe 4-aminobiopterin compounds as inhibitors of NOS. Compounds disclosed in WO 01/21619 are characterized by a substituent(s) at the 4-amino group (preferably alkyl residues) together with a lipophilic side chain at position 6. These compounds are found to be potent inhibitors of NOS.

Inhibition of NOS was also found for 7,8-dihydropteridines (see EP 0 906 913 A1 or U.S. Pat. No. 5,922,713). According to these patent documents, it was shown that the dihydro compounds are more effective in cultivated intact cells than their corresponding tetrahydropteridines. Furthermore, dihydropteridines provide for an increased chemical stability when compared with tetrahydropteridine compounds. However, it is still desirable to have alternative compounds available in order to increase the number of potential drug candidates which have improved inhibitory activity or improved pharmacological properties.

Therefore, the present invention provides novel compounds of formula (I)

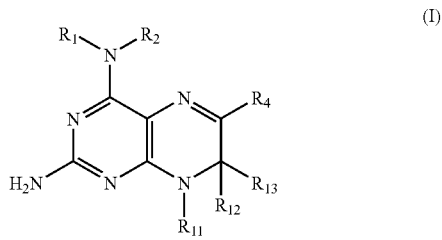

wherein $R_1$ is hydrogen, $(C_1-C_{20})$-alkyl, $(C_1-C_{20})$-alkenyl, $(C_1-C_{20})$-alkynyl, preferably $(C_1-C_{10})$-alkyl, cycloalkyl, cycloalkenyl, preferably $(C_3-C_8)$-cycloalkyl, cycloalkylalkyl, aryl, alkylaryl, preferably $(C_1-C_3)$-alkylaryl or arylalkyl, where the organic radicals, preferably the alkyl and aryl radicals, may be substituted by one or more substituents, preferably by substituents $R_6$, $R_2$ is, independently of $R_1$, hydrogen, $(C_1-C_{20})$-alkyl, $(C_1-C_{20})$-alkenyl, $(C_1-C_{20})$-alkynyl, preferably $(C_1-C_{10})$-alkyl, cycloalkyl, cycloalkenyl, preferably $(C_3-C_8)$-cycloalkyl, cycloalkylalkyl, aryl, alkylaryl, preferably $(C_1-C_3)$-alkylaryl, or arylalkyl, where the organic radicals, preferably the alkyl and aryl radicals, may be substituted by one or more substituents, preferably by substituents $R_6$, or $R_1$ and $R_2$ may, together with the nitrogen atom bearing them, form a 3-8-membered ring which may optionally contain 0, 1 or 2 further heteroatoms from the series N, O, S and which is optionally substituted by one or more radicals, preferably $R_6$ radicals, $R_4$ is $(C_1-C_{20})$-alkyl, $(C_1-C_{20})$-alkenyl, $(C_1-C_{20})$-alkynyl, preferably $(C_1-C_{10})$-alkyl, cycloalkyl, cycloalkenyl, preferably $(C_3-C_8)$-cycloalkyl, cycloalkylalkyl, aryl or $(C_1-C_{20})$-alkylaryl, preferably $(C_1-C_3)$-alkylaryl, arylalkyl, —CO—O-alkyl, preferably —CO—O—$(C_1-C_5)$-alkyl, —CO—O-aryl, —CO-alkyl, preferably —CO—$(C_1-C_5)$-alkyl or —CO-aryl, where the organic radicals, preferably the alkyl and aryl radicals, may be substituted by one or more substituents, in particular by substituents $R_7$, $R_6$ is —F, —Cl, —Br, —I, —OH, —O—$(C_1-C_{10})$-alkyl, —O-phenyl, —O—CO—$(C_1-C_{10})$-alkyl, —O—CO-aryl, —$NR_8R_9$, oxo, phenyl, —CO—$(C_1-C_5)$-alkyl, —$CF_3$, —CN, —$CONR_8R_9$, —COOH, —CO—O—$(C_1-C_5)$-alkyl, —CO—O-aryl, —$S(O)_a$-$(C_1-C_5)$-alkyl, or —$SO_2$-$NR_8R_9$, $R_7$ has, independently of $R_6$, one of the meanings of $R_6$, $R_8$ is hydrogen or $(C_1-C_{20})$-alkyl, preferably $(C_1-C_5)$-alkyl, $R_9$ is hydrogen, $(C_1-C_{20})$-alkyl, preferably $(C_1-C_5)$-alkyl or aryl, preferably phenyl, $R_{11}$ is hydrogen, $(C_1-C_{20})$-alkyl, preferably $(C_1-C_5)$-alkyl, aryl, —CO-alkyl, —CO-aryl, where the organic radicals, preferably the alkyl and/or aryl radicals, may be substituted by one or more substituents, preferably by substituents $R_6$ $R_{12}$ is hydrogen, $(C_1-C_{10})$-alkyl, preferably $(C_1-C_5)$-alkyl, aryl, —O—$(C_1-C_{10})$-alkyl, —O-phenyl, —O—CO—$(C_1-C_{10})$-alkyl, —O—CO-aryl, —$NR_8R_9$, phenyl, —CO—$(C_1-C_{10})$-alkyl, preferably —CO—$(C_1-C_{10})$alkyl, —$CF_3$, —CN, —$CONR_8R_9$, —COOH, —CO—O—$(C_1-C_{10})$-alkyl, preferably CO—O—$(C_1-C_{10})$alkyl, —CO—O-aryl, —F or —Cl $R_{13}$ has, independently of $R_{12}$, one of the meanings of $R_{12}$ aryl is preferably phenyl, naphthyl or heteroaryl, each of which may be unsubstituted or substituted, for example may be substituted by one or more identical or different substituents from the series halogen, $(C_1-C_{20})$-alkyl, preferably $(C_1-C_5)$-alkyl or phenyl, —OH, —O—$(C_1-C_{20})$-alkyl, preferably —O—$(C_1-C_5)$-alkyl, $(C_1-C_{20})$-alkylenedioxy, preferably $(C_1-C_2)$-alkylenedioxy, —$N_8R_9$, —$NO_2$, —CO—$(C_1-C_5)$-alkyl, —$CF_3$, —CN, —$CONR_8R_9$, —COOH, —CO—O—$(C_1-C_5)$-alkyl, —$S(O)_n$-$(C_1-C_5)$-alkyl, —$SO_2$-$NR_8R_9$, heteroaryl is a 5- to 7-membered unsaturated heterocycle which contains one or more heteroatoms from the series O, N, S, n is 0, 1 or 2, in all their stereoisomeric and tautomeric forms and mixtures thereof in all ratios, and their physiologically tolerated salts, hydrates and esters.

with the proviso that compounds of the formula (Ia)

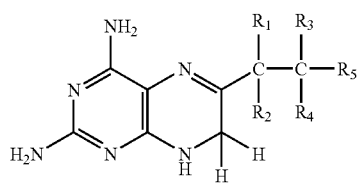

(Ia)

are excluded, wherein in formula (Ia) $R_1$, $R_2$, $R_3$ and $R_4$ are independently from each other H or OH, $R_5$ is H, $CH_3$, $CH_2OH$, CHO or a lower $(C_1-C_9)$ alkyl radical, which can be a straight or a branched chain, as well as $(CH(OH))_n$-Y or $(CH(OH))_n$-$(CH_2)_m$-W, wherein Y is hydrogen or a lower alkyl $(C_1-C_9)$ radical, W is hydrogen or a hydroxyl group, an n and m are independently from each other 1-20.

It has now been found that dihydropteridine derivatives of the formula I, wherein in some embodiments the secondary amino group of the N8 nitrogen atom within the ring system is blocked by a substituent, in particular by a lipophilic side chain, provides for a new class of stable and potent inhibitors of NOS. These compounds as well as the other 4-amino-7,8-dihydropteridine compounds of the invention are thus suitable as pharmaceuticals in diseases which are characterized by an excessive NO level.

In the compounds of formula (I) used in the present invention hereinafter, the following definitions apply, if not stated otherwise.

If groups or substituents occur more than once in the compounds of the formula (I), they may all, independently of one another, have the stated meanings and may in each case be identical or different.

Alkyl radicals in the compounds used in the present invention may be straight-chain or branched. This also applies if they are present in other groups, for example in alkoxy groups, alkoxycarbonyl groups or in amino groups, or if they are substituted. Alkyl radicals normally contain one to twenty carbon atoms, preferably one to ten carbon atoms. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3-dimethylbutyl.

Examples of alkenyl radicals are straight-chain or branched hydrocarbon radicals which contain one or more double bonds. Alkenyl radicals normally contain two to twenty carbon atoms and one or two double bonds, preferably two to ten carbon atoms and one double bond.

Examples of alkynyl radicals are straight-chain or branched hydrocarbon radicals which contain one or more triple bonds. Alkynyl radicals normally contain two to twenty carbon atoms and one or two triple bonds, preferably two to ten carbon atoms and one triple bond.

Examples of alkenyl radicals are the vinyl radical, the 2-propenyl radical (allyl radical), the 2-butenyl radical and the 2-methyl-2-propenyl radical.

Examples of alkynyl radicals are the ethynyl radical, the 2-propynyl radical (propargyl radical) or the 3-butinyl radical.

Cycloalkyl radicals are saturated cyclic hydrocarbons which normally contain three to eight ring carbon atoms, preferably five or six ring carbon atoms. Cycloalkyl radicals may in turn be substituted.

Examples of cycloalkyl radicals are cyclopropyl, cyclobutyl, cyclopentyl, cyclohexyl, cycloheptyl and cyclooctyl, all of which may also be substituted for example by one or more identical or different $(C_1-C_4)$-alkyl radicals, in particular by methyl. Examples of such substituted cycloalkyl radicals are 4-methylcyclohexyl or 2,3-dimethylcyclopentyl.

Cycloalkenyl radicals are unsaturated cyclic hydrocarbons which normally contain three to eight ring carbon atoms, preferably five or six ring carbon atoms. Cycloalkenyl radicals preferably have a double bond in the ring system. Cycloalkenyl radicals may in turn be substituted.

Cycloalkylalkyl radicals are saturated hydrocarbons which are derived from a cycloalkyl-substituted alkyl group. The cycloalkyl group normally has five to six ring carbon atoms. Examples of cycloalkylalkyl radicals are cyclopentylmethyl, cyclopentylethyl, cyclohexyl-ethyl and, in particular, cyclohexylmethyl. Cycloalkylalkyl radicals may in turn be substituted.

Aryl is a carbocyclic or heterocyclic aromatic radical, preferably phenyl, naphthyl or heteroaryl. Aryl radicals may be unsubstituted or substituted. Substituents are one or more identical or different monovalent organic radicals, for example or from the series halogen, alkyl, phenyl, —OH, —O-alkyl, alkylenedioxy, —$NR_8R_9$, —$NO_2$, —CO—($C_1$-$C_5$)-alkyl, —$CF_3$, —CN, —$CONR_8R_9$, —COOH, —CO—O—($C_1$-$C_5$)-alkyl, —$S(O)_n$-($C_1$-$C_5$)-alkyl, —$SO_2$-$NR_8R_9$.

Alkylaryl is an alkyl-substituted aryl radical, preferably ($C_1$-$C_3$)-alkylaryl, in particular methylphenyl.

Arylalkyl is an aryl-substituted alkyl radical, preferably phenylmethyl or 2-phenylethyl.

Heteroaryl or a heterocyclic aromatic radical is preferably a 5- to 7-membered unsaturated heterocycle which has one or more heteroatoms from the series O, N, S.

Examples of heteroaryls from which the radicals occurring in compounds of the formula I may be derived are pyrrole, furan, thiophene, imidazole, pyrazole, 1,2,3-triazole, 1,2,4-triazole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine or 1,3-thiazepine.

The radicals derived from the heterocycles may be bonded via any suitable carbon atom. Nitrogen heterocycles which have a hydrogen atom (or a substituent) on a ring nitrogen atom, for example pyrrole, imidazole, etc, may also be bonded via a ring nitrogen atom, especially if the relevant nitrogen heterocycle is bonded to a carbon atom. A thienyl radical may, for example, be in the form of a 2-thienyl radical or 3-thienyl radical, a furan radical in the form of a 2-furyl radical or 3-furyl radical, a pyridyl radical in the form of a 2-pyridyl radical, 3-pyridyl radical or 4-pyridyl radical.

Halogen is fluorine, chlorine, bromine or iodine, preferably fluorine or chlorine.

In preferred embodiments of formula (I)

$R_1$ is preferably hydrogen, ($C_2$-$C_4$)-alkyl which may be substituted by one or more substituents $R_6$, or ($C_1$-$C_2$)-alkylaryl, and $R_1$ is particularly preferably hydrogen $R_2$ is preferably hydrogen, ($C_2$-$C_4$)-alkyl which may be substituted by one or more substituents $R_6$, or ($C_1$-$C_2$)-alkylaryl, and $R_2$ is particularly preferably hydrogen, cyclohexylmethyl or cyclohexylethyl.

in addition, $R_1$ and $R_2$ preferably form, together with the nitrogen atom bearing them, a 5-7-membered ring which preferably contains no or only one other heteroatom from the series N, O, S. Particularly preferred rings of this type are pyrrolidine, piperidine, morpholine, dimethylmorpholine, thiomorpholine or N—($C_1$-$C_2$)-alkylpiperazine, where these rings themselves may also be substituted, for example by —OH, —O—($C_1$-$C_3$)-alkyl, —$NR_8R_9$ or —COOH.

$R_4$ is preferably aryl, ($C_1$-$C_3$)-alkyl which may be substituted by one or more substituents $R_7$, or —CO—O-aryl. Particularly preferred $R_4$ radicals are 1,2-dihydroxypropyl and aryl, in particular 2-hydroxymethylphenyl.

$R_6$ is preferably —OH, —O—($C_1$-$C_3$)-alkyl, —$NR_8R_9$ or —COOH.

$R_7$ is preferably —OH, —O—($C_1$-$C_{10}$)-alkyl, phenoxy, oxo, particularly preferably —OH, or halogen.

$R_{11}$ is preferably hydrogen, methyl or ethyl $R_{12}$ is preferably hydrogen, methyl, or ethyl $R_{13}$ is preferably hydrogen, methyl or ethyl.

wherein aryl is preferably phenyl, thiophenyl, furyl and pyridyl, and phenyl is particularly preferred, all of which can be substituted as described. Preferred substituents are ($C_1$-$C_3$)-alkyl, halogen and ($C_1$-$C_3$)-alkyloxy and ($C_1$-$C_2$)-alkylenedioxy. The preferred number of substituents on aryl radicals is 0, 1 or 2; phenyl substituents are preferably in the meta or para position, and in the case of two substituents in the 3 and 4 positions.

n is preferably 0 and 2

Particularly preferred is a 7,8-dihydropteridine compound of formula (I) wherein $R_1$ is hydrogen and $R_2$ is hydrogen, alkyl or cycloalkylalkyl and wherein $R_4$ is phenyl, alkylphenyl or alkyl which is optionally substituted with —OH, alkyloxy or halogen and wherein $R_{11}$, $R_{12}$ and $R_{13}$ are independently of each other either hydrogen, methyl or ethyl.

In some embodiments a compound of formula (I) is preferred, wherein $R_1$ is hydrogen, $R_2$ is hydrogen, ($C_1$-$C_{20}$)-alkyl or cycloalkylalkyl, $R_4$ is phenyl, ($C_1$-$C_{20}$)-alkylphenyl or ($C_{12}$-$C_{20}$)-alkyl which is optionally substituted with —OH, alkyloxy or halogen, and wherein $R_{11}$, $R_{12}$ and $R_{13}$ are independently of each other either hydrogen or methyl.

In some of these embodiments, a compound is preferred in which the hydrogen atom at the N8 nitrogen atom of the pteridine ring systems is substituted by an alkyl, aryl or carbonyl substituent.

A particularly suitable class of compounds of formula (I) is represented by those compounds in which $R_1$ is cycloalkyl, cycloalkylalkyl or ($C_1$-$C_{10}$)-alkyl, $R_2$ is hydrogen, $R_4$ is 1,2-dihydroxypropyl and $R_{11}$, $R_{12}$ and $R_{13}$ are independently of each other either hydrogen or methyl.

In this class of compounds, R1 is preferably cyclohexylmethyl or cylcohexylethyl.

In another embodiments a compound of formula (I) is preferred, wherein $R_1$ is hydrogen, $R_2$ is hydrogen, ($C_1$-$C_{20}$)-alkyl or cycloalkylalkyl, $R_4$ is phenyl, ($C_1$-$C_{20}$)-alkylphenyl or ($C_1$-$C_{20}$)-alkyl which is optionally substituted with —OH, ($C_1$-$C_{20}$)-alkyloxy or halogen, $R_{11}$ is ($C_1$-$C_5$)-alkyl, preferably methyl or ethyl, which is optionally substituted, and, $R_{12}$ and $R_{13}$ are independently of each other either hydrogen or ($C_1$-$C_5$)-alkyl, preferably methyl or ethyl, optionally substituted.

Amongst these latter compounds of formula (I), those are preferred in some further embodiments, wherein $R_1$ and $R_2$ are hydrogen, $R_4$ is 1,2-dihydroxypropyl or 2-hydroxymethylphenyl and $R_{11}$ is methyl or ethyl and $R_{12}$ and $R_{13}$ are independently of each other either hydrogen or methyl.

Particularly suitable is such a compound, wherein $R_1$ is cyclohexyl, optionally substituted with ($C_1$-$C_5$)-alkyl, or ($C_1$-$C_5$)—O-alkyl, $R_2$ is hydrogen, $R_4$ is 1,2-dihydroxypropyl and $R_{12}$ and $R_{13}$ are independently of each other either hydrogen or methyl.

Also for these embodiments, a compound has been found to be particularly suitable, wherein $R_1$ is cyclohexylmethyl or cyclohexylethyl.

The compounds of the general formula (I) can be present in various tautomeric forms and in various stereoisomeric forms. The present invention comprises not only all tautomeric forms, but also that of all stereoisomeric forms, i.e., for example, that of pure enantiomers, of enantiomer mixtures and racemates, of pure diastereomers and diastereomer mixtures.

The compounds of the general formula (I) can be prepared according to or analogously to known processes which are described in EP 0 906 913 A1 or U.S. Pat. No. 5,922,713, for example. In a first step of these synthesis routes, the non-reduced compound can be synthesized by known preparative methods for tetrahydropteridines, for example, the method of Gabriel-Isay or the Taylor method (see, for example, D. J. Brown, Fused Pyrimidines III, Pteridines (E. C. Taylor and A. Weissberger (Ed.), Wiley & Sons, New York); Werner et al. Biochem. J. 320 (1996) 193; Schircks et al. Helv. Chim. Acta 60 (1977) 211). As second step, the 7,8-dihydropteridine compound can then be obtained from the corresponding non-reduced tetrahydropteridine by applying the method of Futterman et al. (J. Biol. Chem. 228 (1957) 1031) in combination with the modifications described by Fukishima and Akino (Arch. Biochem. Biophys. 128 (1968) 1). Thereafter, the substituent R11 at the nitrogen in the 8-position can be introduced by acylation as described in WO 01/21619.

Compounds of the invention can also be prepared in accordance with the following synthesis scheme which is based on the method for preparing 7,8-dihydro-pteridines described by Pfleiderer and Mengel in Chem. Ber. 104, 2293-2312 (1971). In the scheme, the substituents R1, R2, R4, R11, R12 and R13 have the meaning as defined above.

In this method the pyrimidine derivative of formula (IV) (for example 2,4-diamino-6-chloro-5-nitro-pyrimidine or the respective N-4-substituted derivative) and a compound of formula (III) such as a ω-methylamino-acetophenone-hydrochloride, are first dissolved in a suitable media such as ethanol, DMF or THF. Then, for the preparation of the 2,4-(substituted)-6-substituted)-triamino-5-nitro-pyrimidine compound (II), a base such as triethylamine is added and the solution is refluxed for a suitable period of time. The reaction is usually carried out at a temperature between ambient temperature and the boiling point of the chosen solvent.

In a second step, the resulting 2,4-(substituted)-6-substituted)-triamino-5-nitro-pyrimidine is then hydrogenated in a solvent such as water, alkaline ethanol/water mixture, THF, or DMF in the presence of a catalyst such as Raney-nickel, platinum dioxide, palladium on charcoal at a hydrogen pressure of about 1 to 200 bar.

The compounds of formula (I) can further be prepared using the following alternative synthesis scheme which is based on the method described by Andrews, K. J. M. et al, Chemical Communications, pages 120-121 (1968). This method is in particular suitable, if the substituent R4 is an alkyl chain which is substituted by one or more hydroxyl groups, for example an 1,2-dihydroxpropyl or 1,2,3 trihydroxpropyl residue.

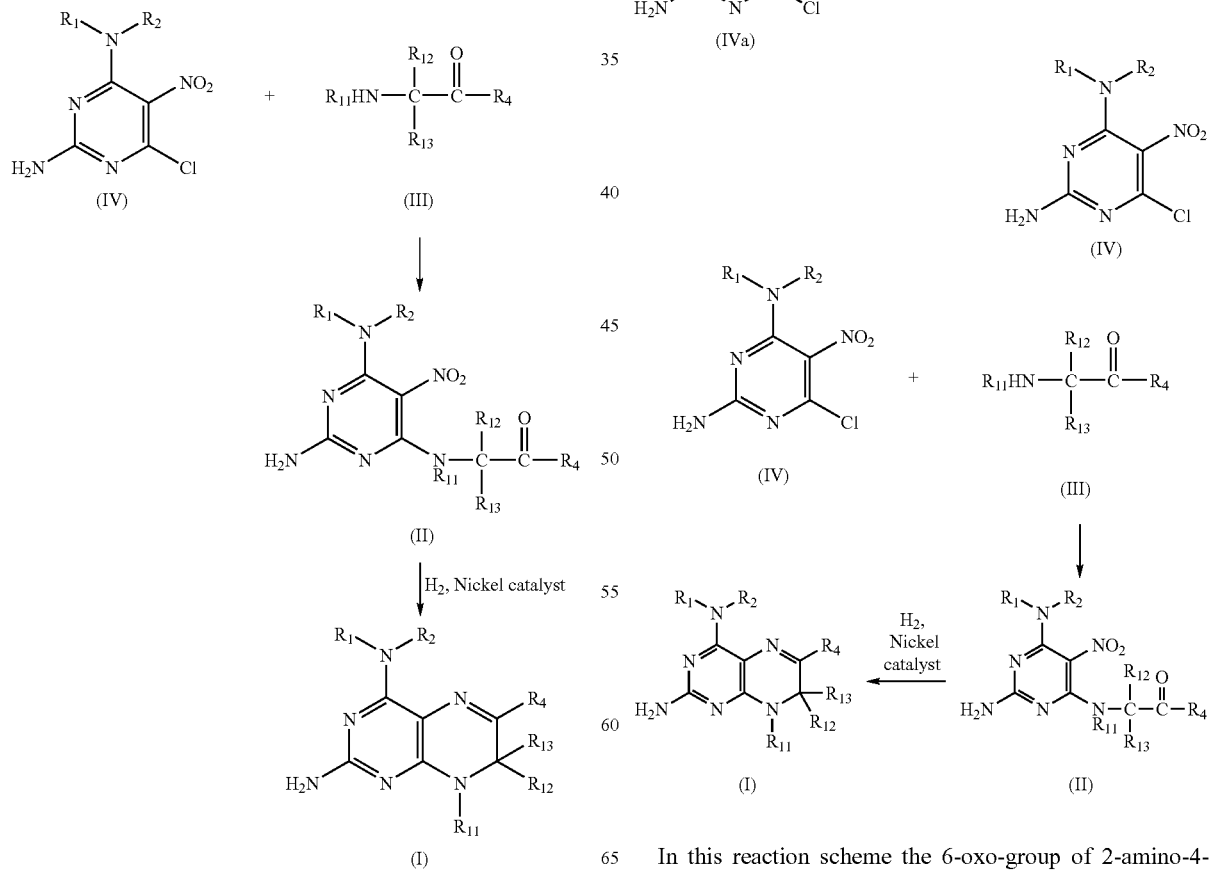

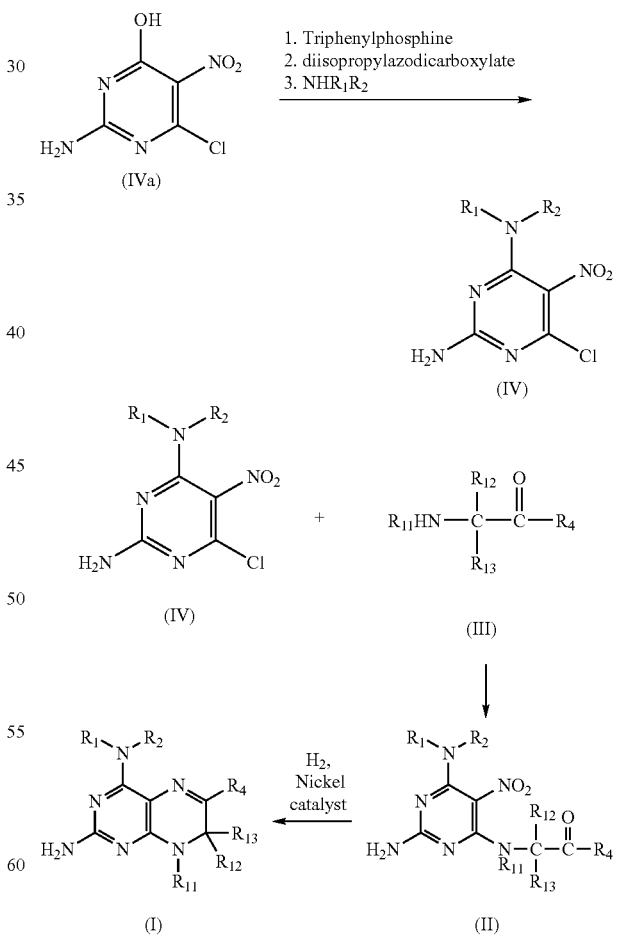

In this reaction scheme the 6-oxo-group of 2-amino-4-chloro-6-hydroxy-5-nitro-pyrimidine (IVa) is replaced by the (substituted) amino group to yield the compound of formula (IV). For this purpose it can be preferably made use of the Mitsunobu reaction (Hanaya T et al, Pteridines (1995) Vol. 6 pp. 1-7). For this purpose, preferably triphenylphosphine and 2-phenylethanol are added to a solution of 2-amino-4-chloro-6-hydroxy-5-nitro-pyrimidine (IVa) in which the amino group has been protected by acetylation. This reaction is usually carried out in a solvent such as 1,4-dioxane. Then diisopropylazodicarboxylate is added to yield the intermediate product 2-amino-4-chloro-5-nitro-$O^6$-2-phenylethyl-pyrimidine, which, after purification by column chromatography (silica, EtOAc/$CH_2Cl_2$ 2:1), is reacted with an amine NHR1R2 in order to obtain a compound of formula (IV). This reaction is preferably performed at a temperature between ambient temperature and the boiling point of the chosen solvent.

In a second step the compound of formula (IV) is first reacted with a compound of formula (III). The reaction conditions can be the same of the scheme explained above. In some embodiments it is useful to employ for the preparation of the intermediate pyrimidine derivative (II) a base such as sodium hydrogen carbonate. The base is added and the solution is refluxed for a suitable period of time. As explained above, the reaction is typically carried out at a temperature between ambient temperature and the boiling point of the chosen solvent.

In a final step the pyrimidine derivative (II) is hydrogenated in order to yield the respective compound of formula (I). Similar to the hydrogenation step in the above synthesis scheme, a solvent such as water, alkaline ethanol/water mixture, THF or DMF is typically employed for this reaction. The reaction is usually carried out in the presence of a catalyst such as Raney-nickel, platinum dioxide, palladium on charcoal at a hydrogen pressure of about 1 to 200 bar.

Another embodiment of the present invention concerns a pharmaceutical composition comprising a pharmaceutically acceptable carrier or diluent and a therapeutically effective amount of at least one of the compounds described hereinbefore.

In yet another embodiment, the present invention relates to the use of 4-amino-7,8-dihydropteridines of the general formula (I)

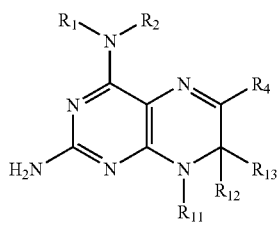

(I)

for treating a disorder characterized by an increased NO level, wherein in formula (I)

$R_1$ is hydrogen, $(C_1-C_{20})$-alkyl, $(C_1-C_{20})$-alkenyl, $(C_1-C_{20})$ alkynyl, preferably $(C_1-C_{10})$-alkyl, cycloalkyl, cycloalkenyl, preferably $(C_3-C_8)$-cycloalkyl, cycloalkylalkyl, aryl, alkylaryl, preferably $(C_1-C_3)$-alkylaryl or arylalkyl, where the organic radicals, preferably the alkyl and aryl radicals, may be substituted by one or more substituents, preferably by substituents $R_6$, $R_2$ is, independently of $R_1$, hydrogen, $(C_1-C_{20})$-alkyl, $(C_1-C_{20})$-alkenyl, $(C_1-C_{20})$-alkynyl, preferably $(C_1-C_{10})$-alkyl, cycloalkyl, cycloalkenyl, preferably $(C_3-C_8)$-cycloalkyl, cycloalkylalkyl, aryl, alkylaryl, preferably $(C_1-C_3)$-alkylaryl, or arylalkyl, where the organic radicals, preferably the alkyl and aryl radicals, may be substituted by one or more substituents, preferably by substituents $R_6$, or $R_1$ and $R_2$ may, together with the nitrogen atom bearing them, form a 3-8-membered ring which may optionally contain 0, 1 or 2 further heteroatoms from the series N, O, S and which is optionally substituted by one or more radicals, preferably $R_6$ radicals, $R_4$ is $(C_1-C_{20})$-alkyl, $(C_1-C_{20})$-alkenyl, $(C_1-C_{20})$-alkynyl, preferably $(C_1-C_{10})$-alkyl, cycloalkyl, cycloalkenyl, preferably $(C_3-C_8)$-cycloalkyl, cycloalkylalkyl, aryl or alkylaryl, preferably $(C_1-C_3)$-alkylaryl, arylalkyl, —CO—O-alkyl, preferably —CO—O—$(C_1-C_5)$-alkyl, —CO—O-aryl, —CO-alkyl, preferably —CO—$(C_1-C_5)$-alkyl or —CO-aryl, where the organic radicals, preferably the alkyl and aryl radicals, may be substituted by one or more substituents, in particular by substituents $R_7$, $R_6$ is —F, —Cl, —Br, —I, —OH, —O—$(C_1-C_{10})$-alkyl, —O-phenyl, —O—CO—$(C_1-C_{10})$-alkyl, —O—CO-aryl, —$NR_8R_9$, oxo, phenyl, —CO—$(C_1-C_5)$-alkyl, —$CF_3$, —CN, —$CONR_8R_9$, —COOH, —CO—O—$(C_1-C_5)$-alkyl, —CO—O-aryl, —$S(O)_n$-$(C_1-C_5)$-alkyl, —$SO_2$-$NR_8R_9$, $R_7$ has, independently of $R_6$, one of the meanings of $R_6$, $R_8$ is hydrogen or $(C_1-C_{20})$-alkyl, preferably $(C_1-C_5)$-alkyl, $R_9$ is hydrogen, $(C_1-C_{20})$-alkyl, preferably $(C_1-C_5)$-alkyl or aryl, preferably phenyl, $R_{11}$ is hydrogen, $(C_1-C_{20})$-alkyl, $(C_1-C_{20})$-alkylaryl, preferably $(C_1-C_5)$-alkyl, aryl, arylalkyl, —CO-alkyl, —CO-aryl, where the organic radicals, preferably the alkyl and/or aryl radicals, may be substituted by one or more substituents, preferably by substituents $R_6$ $R_{12}$ is hydrogen, $(C_1-C_5)$-alkyl, aryl, —O—$(C_1-C_{10})$-alkyl, —O-phenyl, —O—CO—$(C_1-C_{10})$-alkyl, —O—CO-aryl, —$NR_8R_9$, phenyl, —CO—$(C_1-C_5)$-alkyl, —$CF_3$, —CN, —$CONR_8R_9$, —COOH, —CO—O—$(C_1-C_5)$-alkyl, —CO—O-aryl, —F or —Cl $R_{13}$ has, independently of $R_{12}$, one of the meanings of $R_{12}$ aryl is preferably phenyl, naphthyl or heteroaryl, each of which may be unsubstituted or substituted, for example may be substituted by one or more identical or different substituents from the series halogen, $(C_1-C_{20})$-alkyl, preferably $(C_1-C_5)$-alkyl or phenyl, —OH, —O—$(C_1-C_{20})$-alkyl, preferably —O—$(C_1-C_5)$-alkyl, $(C_1-C_{20})$-alkylenedioxy, preferably $(C_1-C_2)$-alkylenedioxy, —$N_8R_9$, —$NO_2$, —CO—$(C_1-C_5)$-alkyl, —$CF_3$, —CN, —$CONR_8R_9$, —COOH, —CO—O—$(C_1-C_5)$-alkyl, —$S(O)_n$-$(C_1-C_5)$-alkyl, —$SO_2$—$NR_8R_9$, heteroaryl is a 5- to 7-membered unsaturated heterocycle which contains one or more heteroatoms from the series O, N, S, n is 0, 1 or 2, in all their stereoisomeric and tautomeric forms and mixtures thereof in all ratios, and their physiologically tolerated salts, hydrates and esters, with the proviso that compounds of the formula (Ia)

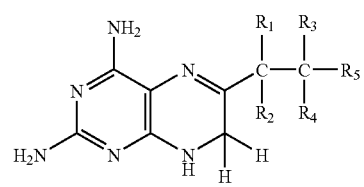

(Ia)

are excluded, wherein in formula (Ia) $R_1$, $R_2$, $R_3$ and $R_4$ are independently from each other H or OH, $R_5$ is H, $CH_3$, $CH_2OH$, CHO or a lower $(C_1-C_9)$alkyl radical, which can be a straight or a branched chain, as well as $(CH(OH))_n$-Y or $(CH(OH))_n$-$(CH_2)_m$-W, wherein Y is hydrogen or a lower alkyl $(C_1-C_9)$ radical, W is hydrogen or a hydroxyl group, an n and m are independently from each other 1-20.

In a preferred embodiment, the present invention relates to the use of 4-amino-7,8-dihydropteridines of the general formula (I) wherein $R_1$ is preferably hydrogen, $(C_2-C_4)$-alkyl which may be substituted by one or more substituents $R_6$, or $(C_1-C_2)$-alkylaryl, and $R_1$ is particularly preferably hydrogen $R_2$ is preferably hydrogen, $(C_2-C_4)$-alkyl which may be substituted by one or more substituents $R_6$, or $(C_1-C_2)$-alkylaryl, and $R_2$ is particularly preferably hydrogen or cyclohexylmethyl in addition, $R_1$ and $R_2$ preferably form, together with the nitrogen atom bearing them, a 5-7-membered ring which preferably contains no or only one other heteroatom from the series N, O, S. Very particularly preferred rings of this type are pyrrolidine, piperidine, morpholine, dimethylmorpholine, thiomorpholine or N—$(C_1-C_2)$-alkylpiperazine, where these rings themselves may also be substituted, for example by —OH, —O—$(C_1-C_3)$-alkyl, —$NR_8R_9$ or —COOH.

$R_4$ is preferably aryl, $(C_1-C_3)$-alkyl which may be substituted by one or more substituents $R_7$, or —CO—O-aryl. Particularly preferred $R_4$ radicals are 1,2-dihydroxypropyl and aryl, in particular 2-hydroxymethylphenyl.

$R_6$ is preferably —OH, —O—$(C_1-C_3)$-alkyl, —$NR_8R_9$ or —COOH.

$R_7$ is preferably —OH, —O—$(C_1-C_{10})$-alkyl, phenoxy, oxo, particularly preferably —OH or halogen.

$R_{11}$ is preferably hydrogen, methyl, or ethyl.

$R_{12}$ is preferably hydrogen, methyl, or ethyl.

$R_{13}$ is preferably hydrogen, methyl, or ethyl.

aryl is preferably phenyl, thiophenyl, furyl and pyridyl, and phenyl is particularly preferred, all of which can be substituted as described. Preferred substituents are $(C_1-C_3)$-alkyl, halogen and $(C_1-C_3)$-alkyloxy and $(C_1-C_2)$-alkylenedioxy. The preferred number of substituents on aryl radicals is 0, 1 or 2; phenyl substituents are preferably in the meta or para position, and in the case of two substituents in the 3 and 4 positions.

n is preferably 0 and 2

As mentioned above, the present invention also encompasses the use of corresponding physiologically or toxicologically acceptable salts, in particular the pharmaceutically usable salts of the compounds according to formula (I).

Thus, the compounds of the formula (I) which contain acidic groups may, for example, be in the form of alkali metal salts, alkaline earth metal salts or of ammonium salts and these groups can be used according to the invention. Examples of such salts are sodium salts, potassium salts, calcium salts, magnesium salts or salts with anunonia or organic amines such as, for example, ethylamine, ethanolamine, triethanolamine or amino acids.

Compounds of the formula (I) which contain one or more basic, that is protonatable, groups may be used in the form of their acid addition salts with physiologically tolerated inorganic or organic acids and used according to the invention, for example as salts with hydrochloric acid, hydrobromic acid, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc.

If a compound according of the formula (I) contain both acidic and basic groups in the molecule, the invention also includes inner salts or betaines (zwitterions) in addition to the salt forms described.

Salts can be obtained from compounds of the formula (I) by conventional processes known to the person skilled in the art, for example by combining with an organic or inorganic acid or base in a solvent or dispersant, or else by anion exchange or cation exchange from other salts. The present invention further encompasses the use of all solvates of compounds of formula (I), for example hydrates or adducts with alcohols, and derivatives of the compounds of the formula (I) such as, for example, esters, and prodrugs and active metabolites.

In accordance with the above disclosure, the present invention is also directed to a method of treating a subject having an increased nitric oxide level comprising administering to the subject a therapeutically sufficient amount of a compound of the general formula (I).

Subjects that are treated are preferably mammals such as humans, monkeys, cats, dogs, mice or rats with humans being preferred.

Diseases which arise due to an increased NO level and which can thus be treated according to the invention with the compounds of the formula I or which can be prevented using these, are, in particular, pathological blood pressure decreases, such as occur in septic or hemorrhagic shock, in tumor or cancer therapy with cytokines or in cirrhosis of the liver. In addition, inflammatory disorders, such as rheumatoid arthritis and in particular ulcerative colitis, as well as insulindependent diabetes mellitus and transplant rejection reactions.

However, the following disorders are also connected with increased production of nitric oxide and can be treated or prevented according to the invention. In the cardiovascular field, these are arteriosclerosis, post-ischemic tissue damage and infarct damage, reperfusion damage, myocarditis based on a Coxsackie virus infection and cardiomyopathy; in the nervous system/central nervous system field they are stroke, multiple sclerosis, traumatic brain injury, neuritides of varying etiogeneses (forms of neuritis), encephalomyelitides, viral neurodegenerative disorders, Alzheimer's disease, hyperalgesia, epilepsy and migraine; in the kidney field they are acute kidney failure and nephritides of varying etiogeneses, especially glomerulonephritis.

Additionally, treatments in the stomach and the uterus/placenta field and also affecting sperm motility are also fields of use for the compounds of the formula I.

For lowering the increased NO level, the compounds of formula (I) can be administered orally, for example in the form of pills, tablets, film-coated tablets, sugar-coated tablets, granules, hard and soft gelatin capsules, aqueous, alcoholic or oily solutions, syrups, emulsions or suspensions, or rectally, for example in the form of suppositories.

The administration can also take place parenterally, for example subcutaneously, intramuscularly or intravenously in the form of injection solutions or infusion solutions. Further suitable administration forms are, for example, percutaneous or topical administration, for example in the form of ointments, tinctures, sprays or transdermal therapeutic systems, or inhalational administration in the form of nasal sprays or aerosol mixtures, or, for example, microcapsules, implants or rods. One preferred mode of administration, especially in case of emergencies, is by injection or infusion in an aqueous pharmaceutically acceptable solution.

The corresponding pharmaceutical compositions that are used according to the invention can be produced by the standard processes known for producing pharmaceutical products.

For this purpose, one or more compounds of the formula (I) and/or their physiologically tolerated salts, esters and hydrates are converted together with one or more solid or liquid pharmaceutical carriers and/or additives or excipients and, if desired, in combination with other active pharmaceutical ingredients with therapeutic or prophylactic action into a suitable administration form or dosage form, which can then be used as pharmaceutical in human medicine or veterinary medicine. The pharmaceutical products comprise a therapeutically or prophylactically effective dose of the compounds of the formula (I) and/or their physiologically tolerated salts, esters and hydrates, which normally amounts to from 0.5 to 90% by weight of the pharmaceutical product.

To produce, for example, pills, tablets, sugar-coated tablets and hard gelatin capsules it is possible to use lactose, starch, for example corn starch or starch derivatives, talc, stearic acid or salts thereof etc. Carriers for soft gelatin capsules and suppositories are for example fats, waxes, semisolid and liquid polyols, natural or hydrogenated oils etc. Examples of carriers suitable for producing solutions, for example injection solutions, or emulsions or syrups are water, physiological saline, alcohols such as ethanol, glycerol, polyols, sucrose, invert sugar, glucose, mannitol, cyclodextrine, vegetable oils etc. The compounds of the formula (I) and their physiologically tolerated salts, esters and hydrates may also be lyophilized, and the resulting lyophilizates can be used together with a reconstitution solution, for example, for producing products for injection or products for infusion. Examples of carriers suitable for microcapsules, implants or rods are copolymers of glycolic acid and lactic acid.

The pharmaceutical products may besides the active ingredients and carriers also comprise conventional additives, for example fillers, disintegrants, binders, lubricants, wetting agents, stabilizers, emulsifiers, dispersants, preservatives, sweeteners, colorants, flavoring or aromatizing agents, thickeners, diluents, buffer substances, also solvents or solubilizers or means to achieve a depot effect, salts to alter the osmotic pressure, coating agents or antioxidants.

The dosage of the active ingredient of the formula I to be administered, and/or of a physiologically tolerated salt, ester or hydrate thereof depends on the individual case and should be adapted to the individual circumstances for an optimal effect in the conventional way. Thus, it depends on the nature and severity of the disease to be treated and on the sex, age, weight and individual response of the human or animal to be treated, on the potency and duration of action of the compounds employed, or on whether other active ingredients are administered in addition to compounds of the formula I. In general, a daily dose of about 0.01 to 100 mg/kg, preferably 1 to 50 mg/kg, in particular 10 to 25 mg/kg (in each case mg per kg of body weight) is appropriate on administration to an adult weighing about 75 kg to achieve the desired effect. The daily dose may be administered in a single dose or, especially on administration of larger amounts, be administered as an intravenous infusion or be divided into a plurality of, for example two, three or four, single doses. It may, depending on the individual characteristics, be necessary where appropriate to deviate upward or downward from the stated daily dose. Pharmaceutical products normally contain 0.2 to 2000 mg, preferably 100 to 1000 mg, of an active ingredient of any of the formula (I) and/or its physiologically tolerated salts.

The present invention will be further illustrated by the following non-limiting Examples.

EXAMPLE 1

1.1. Preparation of 2,4-diamino-8-methyl-6-phenyl-7,8-dihydropteridine 2,4-diamino-8-methyl-6-phenyl-7,8-dihydropteridine as an example for an pteridine compound of the invention carrying an alkyl substitution at the N8 atom can be synthesized in accordance with the following protocol.

Suitable amounts of 2,4-diamino-6-chloro-5-nitro-pyrimidine, for example 6 g and ω-methylamino-acetophenone-hydrochloride, for example 11.8 g can be dissolved in an appropriate solvent, for example 200 ml boiling ethanol. Then an appropriate amount of triethylamine, for example 16 ml, is added and the solution is refluxed for an suitable time, leading to the precipitation of 2,6-diamino-4-[methyl-phenacyl-amino]-5-nitro-pyrimidine. The precipitate is filtered from the solution, washed with a solvent such as ethanol and ether, dried and purified. The purification may be carried out by dissolving the crude product in boiling dimethylformamide, filtering the solution and mixing with a precipitating solvent such as ethanol.

Then 1 g of the purified 2,6-diamino-4-[methyl-phenacyl-amino]-5-nitro-pyrimidine is dissolved in an suitable solvent such as ethanol which has been alkalised by addition of NaOH. 2,6-diamino-4-[methyl-phenacyl-amino]-5-nitro-pyrimidine can then be reduced with Raney-nickel and hydrogen gas until three equivalents of hydrogen are consumed. The catalyst is filtered off and the solution neutralized, for example, with acetic anhydride and cooled overnight at −20° C. The precipitated 4-amino-8-methyl-6-phenyl-7,8-dihydropteridin is filtered, dried and can be purified by re-crystallization, for example.

1.2. Preparation of 2-amino-4-N-cyclohexylmethylamino-6-(L-erythro-1,2-dihydroxypropyl)-7,8-dihydro-pteridine In a first step, 2-Amino-4-chloro-6-N-cyclohexylmethylamino-5-nitro-pyrimidine can be prepared starting from 2-amino-4-chloro-6-hydroxy-5-nitro-pyrimidine using the Mitsunobu reaction as described in Hanaya T et al, Pteridines (1995) Vol. 6 pp. 1-7 (see also Example 2.2b)

A suitable amount of 2-amino-4-chloro-6-hydroxy-5-nitro-pyrimidine, for example 5 mmol, is mixed with acetic anhydride (20 ml) and a solvent such as pyridine (40 ml) and this mixture is then heated to an appropriate temperature such as 100° C. till completion of the reaction. After the starting material has disappeared as judged by TLC, the mixture is evaporated to dryness and the residue chromatographed on silica gel using a suitable eluent such as dichloromethane (DCM) to DCM:MeOH (95:5) in order to obtain the product 2-$N^2$-acetylamino-4-chloro-6-hydroxy-5-nitro-pyrimidine.

Suitable molar amounts of triphenylphosphine and 2-phenylethanol are then sequentially added to a solution of 2-$N^2$-acetylamino-4-chloro-6-hydroxy-5-nitro-pyrimidine in a solvent such as 1,4-dioxane (cf. also Example 2.2b). Diisopropylazodicarboxylate is added dropwise to this mixture and the reaction mixture then stirred, usually at room temperature for a suitable period of time. The resulting intermediate product carrying the $O^6$-2-phenylethyl group at the 6-position can be purified by column chromatography on silica gel, using an appropriate eluent such as dichloromethane (DCM): AcOEt (1:2) followed by AcOEL The reaction mixture so obtained can be reacted with cyclohexylmethylamine in 1,4-dioxane (20 ml) under reflux for 2 h. This volume of the reaction is then reduced, and concentrated ammonia is added and the mixture stirred for another suitable time period such as 18 h. The so obtained 2-amino-4-chloro-6-N-cyclohexylmethylamino-5-nitro-pyrimidine can be isolated from the reaction mixture by evaporation of the solvent and chromatography of the residue on silica gel.

2-Amino-4-chloro-6-N-cyclohexylmethylamino-5-nitro-pyrimidine and 1-amino-1,5-dideoxy-L-erythro-pentulose are reacted in aqueous alcohol in the presence of sodium hydrogen carbonate as described in Andrews et al., Chemical Communications, pages 120-121 (1968) to yield the corresponding nitropyrimidinyl-aminoketose. This aminoketose is then hydrogenated in water or an ethanol/aqueous NaOH mixture, using Raney nickel as catalyst to produce 2-amino-4-N-cyclohexylmethylamino-6-(L-erythro-1,2-dihydroxypropyl)-7,8-dihydro-biopteridin. The crude product can then be precipitated, for example by addition of glacial acetic acid or any other suitable precipitating agent and further purified by chromatography.

The use of 1-N-alkylamino-1,5-dideoxy-L-erythro-pentulose or 1-N-arylamino-1,5-dideoxy-L-erythro-pentulose instead of 1-amino-1,5-dideoxy-L-erythro-pentulose leads to compounds with an alkyl or aryl substituted N8-nitrogen atom.

EXAMPLE 2

In vivo stability of 4-N-substituted-7,8-dihydropteridines

2.1 Determination of in vivo stability

The compounds 4-N-cyclohexylmethylamino-5,6,7,8-tetrahydrobiopterin (compound A), 2-amino-4-piperidino-6-phenyl-(R,S)-5,6,7,8-tetrahydropteridin (compound B) and 2-amino-4-di-n-propylamino-6-(4-methoxyphenyl)-(R,S)-5,6,7,8-tetrahydropteridin (compound C) were intravenously injected into male Sprague-Dawley rats (1-10 mg/kg). Venous blood samples were taken up to eight hours after the injections and analyzed for the injected tetrahydro-compounds and for their corresponding dihydro-derivatives, which are spontaneously formed in vivo, by LC-MS/MS. While the tetrahydro-compounds were oxidized with a half-life time of less than 5 minutes, the corresponding dihydro-compounds were cleared from the bloodstream at significantly slower rates (see table 1):

TABLE 1

Half-life for blood clearance of compounds of the invention in male Sprague-Dawley rats

| compound | $t_{1/2}$ (tetrahydro) | $t_{1/2}$ (dihydro) |
|---|---|---|
| A | <<5 min | 48 min |
| B | <<5 min | ~20 min |
| C | <<5 min | ~30 min |

EXAMPLE 2.2

Preparation of 5,6,7,8 tetrahydropteridine compounds a) Synthesis of 2-amino-4-piperidino-6-phenyl-(R, S)-5,6,7,8-tetrahydropteridin (Compound B) and 2-amino-4-di-n-propylamino-6-(4-methoxyphenyl)-(R,S)-5,6,7,8-tetrahydropteridin (Compound C)

2-amino-4-piperidino-6-phenyl-(R,S)-5,6,7,8-tetrahydropteridin and 2-amino-4-di-n-propylamino-6-(4-methoxyphenyl)-(R,S)-5,6,7,8-tetrahydropteridin were prepared as described in Matter et al., Journal of Medical Chemistry, 2002, 45, 14, pages 2923-2941 or WO 01/21619.

b) Synthesis of 4-N-cyclohexylmethylamino-5,6,7,8-tetrahydrobiopterin (Compound A)

1. Synthesis of tri-$N^2$,1',2'—O-acetyl-L-biopterin

Biopterin (1 g, 4.21 mmol) dissolved in pyridine (40 ml) and acetic anhydride (20 ml) was heated to 100° C. After 3 h, the starting material disappeared as judged by TLC, the mixture was evaporated to dryness and the residue was chromatographed on silica gel eluting with dichloromethane (DCM) to DCM:MeOH (95:5). The product tri-$N^2$, 1, 2'—O-acetyl-L-biopterin was obtained as brown foam in quantitative yield (1.5 g). The product was characterized by NMR and mass spectrometry:

NMR (DMSO-D6): 12.32 (1H, s, NH), 12.01 (1H, s, NH), 8.95 (1H. s, H-7). 5.93 (1H, d, J=4.2 Hz, H-1'), 5.34 (1H, dq, J=6 and 4 Hz, H-2'), 2.20 (3H, s, Ac); 2.16 (3H, s, Ac), 1.96 (3H, s, Ac), 1.19 (3H, d, J=6.9Hz, $CH_3$,-3'). MS (APCI): 364 $[M+H]^+$ 2. Synthesis of tri-$N^2$,1,2'—O-acetyl-$O^4$-2-phenylethyl-L-biopterin Triphenylphosphine (1.2 g, 5.4 mmol) and 2-phenylethanol (0.65 g, 5.4 mmol) were sequentially added to a solution of tri-$N^2$,1,2'-O-acetyl-L-biopterin (1.5 g, 4.21 mmol) in 1,4-dioxane (7 ml). To this mixture diisopropylazodicarboxylate (1.05 ml, 5.4 mmol) was added dropwise and the reaction mixture was stirred at room temperature for 18 h. Evaporation and column chromatography on silica gel eluting with AcOEt (1:2) followed by AcOEt gave the expected product together with triphenylphosphine oxide.

3. Synthesis of 4-N-cyclohexylmethylamino-4-desoyx-L-biopterin

The reaction mixture obtained in step 2 was then heated with cyclohexylmethylamine (2.2 ml, 16.8 mmol) in 1,4-dioxane (20 ml) under reflux for 2 h. This volume of the reaction was reduced by 50% by evaporation and concentrated ammonia (32%) (30 ml) was then added. Thereafter, the mixture was stirred for 18 h. The reaction mixture was evaporated and chromatographed on silica gel eluting with dichloromethane DCM:MeOH (9:1) to DCM:MeOH:$NH_4OH$ (90:10:1) to get the expected product as a yellow solid (0.9 g, 64% yield). The product was characterized by NMR and mass spectrometry.

NMR (DMSO-D6): 8.70 (1H, s, H-7), 8.10 (1H, t, J=6.3 Hz, NH), 6.60 (2H, s, NH2), 5.42 (1H, br s, OH), 4.65 (1H, br s, OH), 4.40 (1H, d, J=3.9 Hz, H-1'), 3.81 (H, m, H-2'), 3.34 (2H, m, CH2). 1.71 (5H, m, cyclohexyl), 0.95-1.27 (6H, m, cyclohexyl), 1.13 (3H, d, J=6.3 Hz, $CH_3$-3). MS (APC1: 333 $[M+H]^+$ 4. Synthesis of 4-N-cyclohexylmethylamino-5,6,7,8-tetrahydrobiopterin 4-N-Cyclohexylmethylamino-4-deoxy-L-biopterin (1.1 g, 3.3 mmol) dissolved in trifluoracetic acid (15 ml, TFA) was added to a suspension of $PtO_2$ (0.18 g) in TFA (10 ml) previously hydrogenated to metallic platinum. The reaction mixture was hydrogenated for 3 h, filtered through celite and evaporated. The residue was dissolved in HCl (1.25 M in methanol) (20 ml) and stirred overnight. Evaporation to dryness and trituration with AcOEt gives the expected product by filtration as a green powder (1.3 g, 97% yield). The product was characterized by NMR, mass spectrometry and elemental analysis.

NMR (CDC13-CD30D): 3.80-3.95 (SH, m), 2.78 (1H, d, J=6.9 Hz), 0,9-1.8 (1611, m). MS (APC1): 337 [M+]+. Anal. ($l_{16}H_{28}N_6O_2 \times 2$ HCl after drying); calculated: 46.95% C, 7.39% H, 20.53% N, 17.32% Cl. Found: 47.11% C, 7.36% H, 20.51% N, 17.08% Cl. The water content was calculated to be 8.15% before drying. The water content increased after five successive measurements as follows: 8.15, 8.70, 10.71, 11.28, and 11.53% (showing the hygroscopicity of the compound).

EXAMPLE 3

Inhibition of NO Release

The inhibition of NO release by the compounds of the general formula (I) can be determined by an activity assay based on the studies of Knipp und Vasak (Analytical Biochemistry 286, 257-264 (2000)). In this assay for purified NO synthase (NOS) the coproduct L-citrulline obtained during NO formation is determined quantitatively. This is carried out by the use of the color developing reaction between the carbamide group of citrulline with the reagents diacetyl-monoxime. and thiosemicarbazide. After this reaction, the colored product can be quantified directly by measuring the absorbance at 540 nm.

In this assay, 60 μl of substrate-cofactor-mix (1 mM $CaCl_2$, 1 mM $MgCl_2$, 1 mM arginine, 1 mM β-nicotinamide adenine dinucleotide phosphate, 5 μM flavin adenine dinucleotide, 5 μM riboflavin 5'-monophosphate, 2 μM tetrahydrobiopterin in HEPES, 100 mM, pH 7.4), 2 μl of a compound of formula (I) in dimethylsulfoxide and 0.5 or 1 μl of the purified enzyme NOS are incubated for two hours at 37° C. Then, 100 μl of the colour developing reagent mix (20 mM diacetyl-monoxime, 0,5 mM thiosemicarbazide, 4,5 M $H_2SO_4$, 2,25 M $H_3PO_4$, 1,5 mM $NH_4Fe(SO_4)_2$) are added, the samples are incubated for 15 minutes at 95° C. and subsequently centrifuged for 10 minutes at >1000 g. During the centrifugation, the samples cool down to room temperature. 130 μl of each supernatant are transferred into low-volume 96-well-plates and the absorbance at 540 nm is measured. Comparison with values from uninhibited NOS (100%-values) and samples containing no enzyme (0-values) yields the inhibitor-effect of each tested compound.

The invention claimed is:

1. A compound of formula I, stereoisomeric and tautomeric forms and mixtures thereof, and physiologically tolerated salts, and esters thereof:

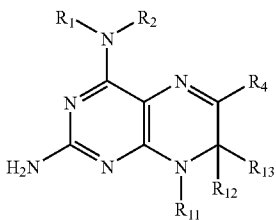
(I)

wherein:
$R_1$ is chosen from hydrogen,
$R_2$ is chosen from, independently of $R_1$, hydrogen, ($C_1$-$C_{20}$)-alkyl, and cycloalkylalkyl,
$R_4$ is chosen from phenyl, ($C_1$-$C_{20}$)-alkylphenyl, and ($C_2$-$C_{20}$)-alkyl, which is optionally substituted with —OH, alkyloxy or halogen,
$R_{11}$ is chosen from ($C_1$-$C_5$)-alkyl, which is optionally substituted,
$R_{12}$ and $R_{13}$ are independently chosen from hydrogen, and ($C_1$-$C_5$)-alkyl, which is optionally substituted.

2. The compound of claim 1, wherein:
$R_1$ is hydrogen,
$R_2$ is chosen from hydrogen, ($C_1$-$C_{20}$)-alkyl and cycloalkylalkyl,
$R_4$ is chosen from phenyl, ($C_1$-$C_{20}$)-alkylphenyl and ($C_{12}$-$C_{20}$)-alkyl which is optionally substituted with —OH, alkyloxy or halogen,
$R_{11}$ is methyl, and
$R_{12}$ and $R_{13}$ are independently of each other chosen from hydrogen and methyl.

3. The compound of claim 1, wherein:
$R_1$ and $R_2$ are hydrogen,
$R_4$ is 1,2-dihydroxypropyl
$R_{11}$ is chosen from methyl and ethyl, and
$R_{12}$ and $R_{13}$ are independently of each other chosen from hydrogen and methyl.

4. A pharmaceutical composition comprising a pharmaceutically acceptable carrier or diluent and a therapeutically effective amount of a compound according to claim 1, or a pharmaceutically acceptable acid addition salt thereof.

* * * * *